United States Patent [19]
Tsuno

[11] Patent Number: 4,640,577
[45] Date of Patent: Feb. 3, 1987

[54] IMAGE FIBER WITH A MECHANISM FOR ROTATING A FIELD OF VIEW

[75] Inventor: Koichi Tsuno, Osaka, Japan

[73] Assignee: Sumitomo Electric Industries, Ltd., Osaka, Japan

[21] Appl. No.: 767,069

[22] Filed: Mar. 19, 1985

Related U.S. Application Data

[63] Continuation-in-part of Ser. No. 503,475, Jun. 13, 1983, abandoned.

[30] Foreign Application Priority Data

Jun. 11, 1982 [JP] Japan ................................ 57-100349

[51] Int. Cl.⁴ .............................................. G02B 7/04
[52] U.S. Cl. ............................... 350/96.25; 350/96.18; 350/96.10

[58] Field of Search ............... 350/96.18, 96.15, 96.24, 350/96.25

[56] References Cited

U.S. PATENT DOCUMENTS 4,261,638  4/1981  Wagner .......................... 350/96.15

Primary Examiner—William L. Sikes
Assistant Examiner—Akm Ullah
Attorney, Agent, or Firm—Sughrue, Mion, Zinn, Macpeak and Seas

[57] ABSTRACT

In an inspection device having a light guide, an image fiber and a mirror for reflecting light from the light guide to an object and for reflecting an image of the object to the image fiber, the mirror is rotatable about an axis coincident with the optical axis at the end of the image fiber.

10 Claims, 5 Drawing Figures

IMAGE FIBER WITH A MECHANISM FOR ROTATING A FIELD OF VIEW

CROSS REFERENCE TO RELATED APPLICATIONS

This patent application is a continuation-in-part of pending U.S. patent application Ser. No. 503,475, filed June 13, 1983 for an image fiber with a mechanism for rotating a field of view, now abandoned.

BACKGROUND OF THE INVENTION

The present invention relates to an image fiber with a mechanism for rotating a field of view which is used, for example, to inspect the inner surface of a pipe for potential damage.

A conventional image fiber with a mechanism for rotating a field of view is shown in FIG. 1. The invention comprises a main portion 5 and a flexible tube 1 in which there is provided in parallel an image fiber 2 and a light guide 3. The ends of the image fiber and the light guide 3 are retained by a cap 4 and the mechanism for rotating a field of view, hereinafter referred to as an adapter 6. The adapter 6 is detachably mounted onto the main portion 5 and is comprised of a motor 7 provided with a rotary shaft which is substantially parallel to the axis of the image fiber 2, a 45° mirror 8 which is arranged in such a way as to be opposite to the ends of the image fiber 2 and the light guide 3 and which is mounted onto the rotary shaft of the motor 7, and a cylindrical transparent window 9 for transmitting therethrough an illuminating light reflected from the mirror 8 and for receiving therethrough an image.

FIG. 1 also shows an object 10 which is illuminated with light from a light source (not shown) via the light guide 3. The image of the object 10 is reflected back to the image fiber 2 through the cylindrical transparent window 9 via the mirror 8 and an image pickup lens 11. If the mirror 8 is rotated by means of the motor 7, as indicated by the arrows in the drawing, it becomes possible to observe the entire inner surface of the pipe. In FIG. 1, reference numeral 12 denotes a nut for adjusting the focus and reference numeral 13 denotes a lock nut for locking the focusing adjustment.

Because the axis 2a of the image fiber 2 differs from the rotational axis 8a of the 45° mirror 8 by δ, as shown in FIG. 2, the position of the image of the object 10 (the inner surface of a pipe) which is reflected to the image fiber deviates by 2δ along the longitudinal direction of the object 10 when the mirror takes positions which are different from each other by 180° (as indicated by the solid and dotted lines in FIG. 2). The above mentioned difference between the axis 2a of the image fiber and the rotational axis 8a of the 45° mirror results from the image fiber 2 and the light guide 3 being symmetrically arranged on both sides of the cylindrical axis of the main portion 5 in order to minimize the outer diameter of the main portion 5.

The nearer the object is with respect to the mirror, for example in pipes with small inner diameters, the more outstanding the deviation of the position of the image of the object becomes. Additionally, there is a further drawback in that because of the reflection of the illuminating light by the transparent window 9 it becomes difficult to view the object.

SUMMARY OF THE INVENTION

It is an object of the present invention to provide an image fiber with a mechanism for rotating a field of view which overcomes the drawbacks of the prior art.

The present invention is comprised of a main portion which is provided with an image fiber and a light guide, in parallel relation to each other. A mechanism for rotating a field of view is detachably mounted to the end of the main portion and is comprised of a motor with a rotary shaft, a mirror used for reflecting an illuminating light and an image and is mounted onto the rotary shaft of the motor in such a way as to form a predetermined angle with respect to the rotary shaft. The mirror is also arranged so as to have its reflecting surface opposite to the ends of the image fiber, light guide and a window for reflecting the illuminating light therethrough and for receiving therethrough the image. One improvement of the present invention is that the rotary shaft of the motor is aligned with the axis of the image fiber in order to prevent deviation in the position of the image of the object when the mirror is rotated to different positions. A second improvement is that the window is an opened window formed in the side surface of the mechanism for rotating a field of view in order to prevent the reflection of illuminating light by the window when viewing an object.

DETAILED DESCRIPTION OF THE INVENTION

Figure 1:
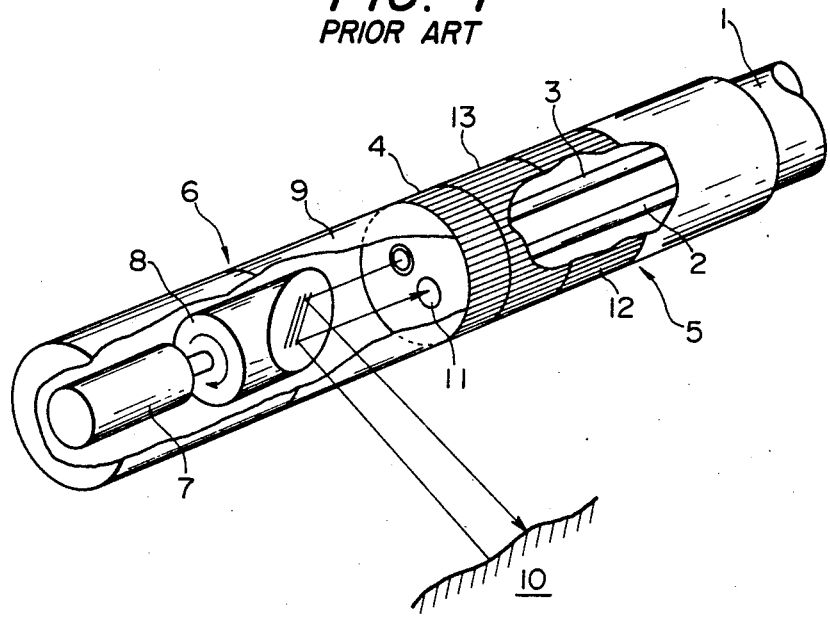
FIG. 1 is a partially cut-away perspective view showing an image fiber with a mechanism for rotating a field of view in accordance with the prior art.
Figure 2:
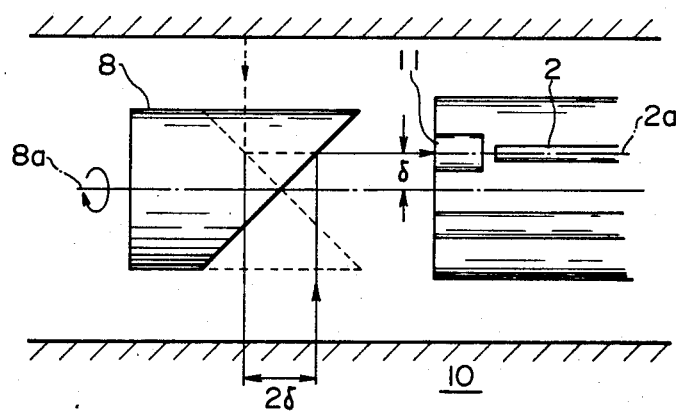
FIG. 2 shows the relationship between movement of the field of view and the eccentricity of the image fiber.
Figure 3:
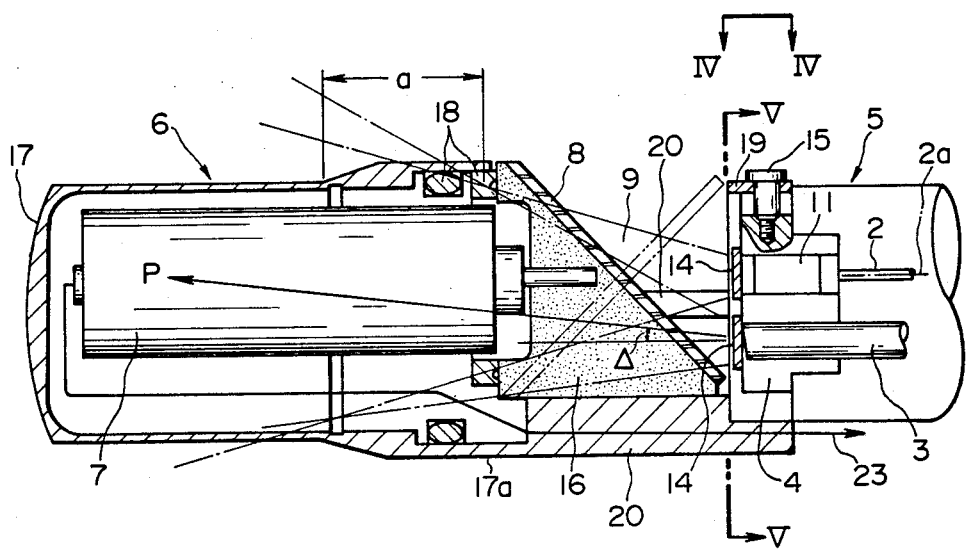
FIG. 3 is a cross-sectional view showing an embodiment of the present invention.

An explanation with reference to the accompanying figures will be given below of the preferred embodiment of the present invention. As can be seen in FIG. 3, which is a cross-sectional view showing the preferred embodiment of the present invention, an image fiber is comprised of a main portion 5 which contains an image fiber 2 and a light guide 3 in parallel relation with each other. The image fiber further includes a mechanism for rotating a field of view, hereinafter referred to as an adaptor 6, which is detachably mounted to the end of the main portion 5. There is also provided a cap 4 which has holes into which are fitted ends of the image fiber 2 and the light guide 3 so that they are retained at the end of the main portion 5. An image pickup lens 11 is optically connected to the image fiber 2 in the hole into which is fitted the end of the image fiber 2. Each of the above described holes is sealed in a watertight manner by a transparent material 14 such as a glass plate or the like. In addition, there are provided a plurality of screws 15 on the outer peripheral part of the cap 4 in such a manner that they are distant from one another in the circumferential direction. The plurality of screws form a portion of a one-touch mounting mechanism for the adaptor 6 which will be described later.

The adaptor 6 is comprised of a motor 7 which has its rotary shaft aligned with the axis 2a of the image fiber 2, and a mirror 8 for reflecting an illuminating light and an image. In FIG. 3, reference numeral 23 denotes a lead wire to the motor 7. The mirror 8 is formed by evaporating the inner side (back surface) of a glass. The mirror 8 is mounted so as to form a predetermined angle (usually 45°) with respect to the rotary shaft of the motor and is connected to the rotary part of the motor via a mirror support member 16. The mirror is further arranged so that its reflecting side is opposite to the ends of the image fiber 2 and the light guide 3 and also opposite a window 9 which allows the illuminating light and the image to pass therethrough.

The motor 7 is maintained in a housing 17. O-rings 18 are used as seals between the motor 7 and the housing 17 and between the mirror support member 16 and the housing 17 so as to provide a structure which is water-resistant. In addition, the above described window 9 is formed as an opened window in a portion of side wall 17a of the housing 17. The window opening is formed so as to leave a ring 19, shown in FIG. 4, at the rear end of the side wall 17a of the housing 17 and with three window frames 20 which extend in the axial direction between the ring 19 and the housing proper, as shown in FIGS. 3 and 5. The three window frames 20 are provided so that one of the ridgelines closely approaches the side surface of the mirror 8, as shown in FIG. 5, thereby preventing any extraneous substance from entering between the mirror 8 and the window frames 20. As illustrated in FIGS. 3 and 5 lead wires for the motor 7 passes through one of the window frames 20.

Figure 4:
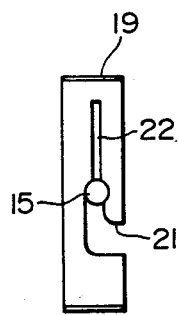
FIG. 4 is a cross-sectional view taken along the IV—IV line in FIG. 3.
Figure 5:
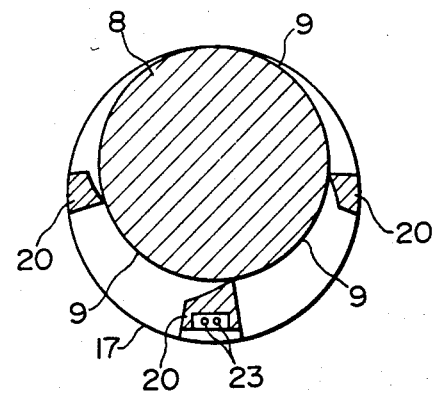
FIG. 5 is a cross-sectional view taken along the V—V line in FIG. 3.

In the ring 19 which is formed at the rear end of the side wall 17a of the housing, there are formed L-shaped grooves 21 of a number (usually two) which correspond to the number of screws 15 which are provided on the cap 4 of the main portion 5 (there is shown only one L-shaped groove 21 in FIG. 4). If the cap 4, at the side of the main portion 5, is inserted into the ring 19 and turned, it becomes possible to effect one-touch mounting between the main portion 5 and the adaptor 6. The main portion 5 and adaptor 6 can be separated from each other by a similar but reverse operation. It is desirable that a slit 22 is formed which communicates with the innermost portion of the L-shaped groove 21, in order to provide a spring function thereto.

The image fiber of the present invention is designed to set a focusing distance (a) for a subject shown in FIG. 3, which corresponds to a focusing distance which would exist if the fiber were looking in the forward direction without a mirror, and the field of view of the image fiber is illuminated by an illuminating light from the light guide 3 within this range. In view of this, the end surface of the light guide is obliquely ground so that the center axis (P) of the light emitted from the light fiber 3 is inclined from the light guide axis, as shown in FIG. 3.

Since the center of rotation of the mirror 8 coincides with the axis 2a of the image fiber 2, the field of view is not shifted in the longitudinal direction when the mirror is rotated. In addition, since window 9 is an open window, there is no reflection of the illuminating light due to the window, thereby making it possible to more clearly view the object. Furthermore, it is easy to mount or separate the main portion 5 and the adaptor 6 by virtue of the one-touch mounting means. Additionally, since the main portion 5 and the adaptor 6 are provided with the water-resistant mechanism, the use of the present invention in a liquid is also possible.

Uses for the present invention include inspecting an inner surface of a pipe, inspecting the inner portion of a machine, and as a medical fiber scope or the like.

As mentioned above, with the present invention it is possible to obtain an image fiber with a mechanism for rotating a field of view in which there is no deviation of the field of view in the longitudinal direction and in which it is possible to clearly observe an object.

What is claimed is:

1. An image fiber device of the type having a mechanism for rotating a field of view, said image fiber device comprising; a main portion, having an image fiber and a light guide parallel to said image fiber, and an adaptor mechanism detachably mounted to the end of said main portion for rotating a field of view of said image fiber device, said adaptor including a window, a motor with a rotary shaft substantially parallel to the axis of said image fiber, a mirror having a reflecting surface for reflecting an illuminating light from said light guide through said window to an object to be viewed and for receiving an image of said object through said window and reflecting said image to said image fiber, said mirror being mounted on said rotary shaft and having its reflecting surface opposite the ends of said image fiber and light guide and opposite said window, the axis of said rotary shaft being coincident with the axis of said image fiber, and said window being opened and formed in a side surface of said adaptor mechanism, at a position adjacent to said reflecting surface of said mirror.

2. An image fiber device as claimed in claim 1 wherein said mirror comprises a mirror made of a glass with an evaporation film formed on the back surface thereof as said mirror.

3. An image fiber device as claimed in claim 1 wherein said adaptor mechanism is assembled into a water-resistant housing.

4. An image fiber device as claimed in claim 1 wherein said main portion is provided with a cap having holes therein for receiving and retaining the ends of respective ones of said image fiber and light guide.

5. An image fiber device as claimed in claim 4, further comprising a transparent material disposed between said mirror and the ends of each of said image fiber and light guide for sealing said holes in a watertight manner.

6. An image fiber device as claimed in claim 1 wherein the end surface of said light guide is obliquely ground so that light emitted from said light guide toward said mirror is inclined with respect to the axis of said light guide.

7. The image fiber device of claim 1 further comprising window frames supporting said mirror, said window frames extending parallel to said axis of said image fiber.

8. The image fiber device of claim 7 wherein said window frames have ridge portions contacting an outer peripheral surface of said mirror, whereby extraneous materials cannot enter between said window frames and said mirror.

9. The image fiber device of claim 7 further comprising lead wires for said motor, said lead wires passing through one of said window frames.

10. The image fiber device of claim 7 wherein three window frames are provided to support said mirror.

* * * * *